United States Patent
Berka et al.

(10) Patent No.: US 6,423,946 B1
(45) Date of Patent: Jul. 23, 2002

(54) APPARATUS FOR AND METHOD OF DEVELOPING FINGERPRINTS

(76) Inventors: Ladislav H. Berka, 14 Walbridge Rd., Paxton, MA (US) 01612; Giacomo P. Ferraro, Jr., P.O. Box 104, 1469 Main St., Leicester, MA (US) 01524; David P. Grady, 40 Colonial Dr., Shrewsbury, MA (US) 01545

(*) Notice: Subject to any disclaimer, the term of this patent is extended or adjusted under 35 U.S.C. 154(b) by 0 days.

(21) Appl. No.: 09/867,011

(22) Filed: May 29, 2001

Related U.S. Application Data

(60) Provisional application No. 60/214,520, filed on Jun. 28, 2000.

(51) Int. Cl.[7] .................................................. F27B 5/05
(52) U.S. Cl. ..................... 219/390; 219/392; 118/31.5; 118/715; 427/255.4
(58) Field of Search .................................. 219/390, 392, 219/405, 411; 392/416, 418; 118/31.5, 715; 427/255.4, 145, 345

(56) References Cited

U.S. PATENT DOCUMENTS

| | | | |
|---|---|---|---|
| 4,297,383 A | | 10/1981 | Bourdon |
| 4,394,773 A | * | 7/1983 | Ruell ............................ 382/4 |
| 4,504,408 A | * | 3/1985 | Morton ................... 252/301.16 |
| 4,550,041 A | * | 10/1985 | Thompson et al. ........... 428/35 |
| 4,556,579 A | * | 12/1985 | Lowell .......................... 427/1 |
| 4,700,657 A | * | 10/1987 | Butland ..................... 118/31.5 |
| 4,719,119 A | | 1/1988 | Thompson et al. |
| 5,079,029 A | | 1/1992 | Saunders |
| 5,266,112 A | | 11/1993 | Crosbie |
| 5,348,159 A | | 9/1994 | Watkin et al. |
| 5,348,759 A | | 9/1994 | Weaver et al. |
| 5,424,092 A | | 6/1995 | Weaver et al. |
| 5,465,765 A | | 11/1995 | Martindale |
| 5,871,804 A | | 2/1999 | Wilkinson et al. |
| 5,974,162 A | * | 10/1999 | Metz et al. ................. 382/124 |

OTHER PUBLICATIONS

Kendall, F.G. "Super Glue Fuming for the Development of Latent Fingerprints", *Identification News*, 32(5), May 1982, pp. 3–5.
Besonen, J.A. "Heat Acceleration of the Super Glue Fuming Method for Development of Latent Fingerprints", *Identification News*, 33(2), Feb. 1983, pp. 3–4.
Lee, H.C.; Gaensslen, R.E. (eds.), *Advances in Fingerprint Technology*, Elsevier, New York, 1991, pp. 67–71.
Watkin, J.E.; Wilkinson, D.A.; Misner, A.H.; Ymashita, A.B., "Cyanoacrylate Fuming of Latent Prints: Vacuum Versus Heat/Humidity", *Journal of Forensic Identification*, 44(5), 1994, pp. 545–556, International Association of Identification, USA.
"Coleman Vacu–Print™ Glue Fuming Vacuum Unit", Lightning Powder Company, Inc., Feb. 1, 1999, pp. 30–31, USA.
"Cyvac™ Systems", *Cyvac™ Vacuum Systems for Fingerprint Development*.

* cited by examiner

Primary Examiner—Teresa Walberg
Assistant Examiner—Shawntina T. Fuqua
(74) Attorney, Agent, or Firm—Blodgett & Blodgett, P.C.

(57) ABSTRACT

An apparatus for and method of developing fingerprints on an object by cyanoacrylate fuming. The apparatus includes a container having a chamber, an opening to the chamber and a mechanism for evacuating air from the chamber. The apparatus also includes a cover for hermetically sealing the opening, an exposed upper surface in the chamber for receiving drops of cyanoacrylate and an electrical heater for heating the exposed upper surface. More specifically, the electrical heater is located in the chamber and supports a receptacle which has the exposed upper surface. The electrical heater has an electrical cord that extends through an airtight fixture which is attached to the cover.

16 Claims, 2 Drawing Sheets

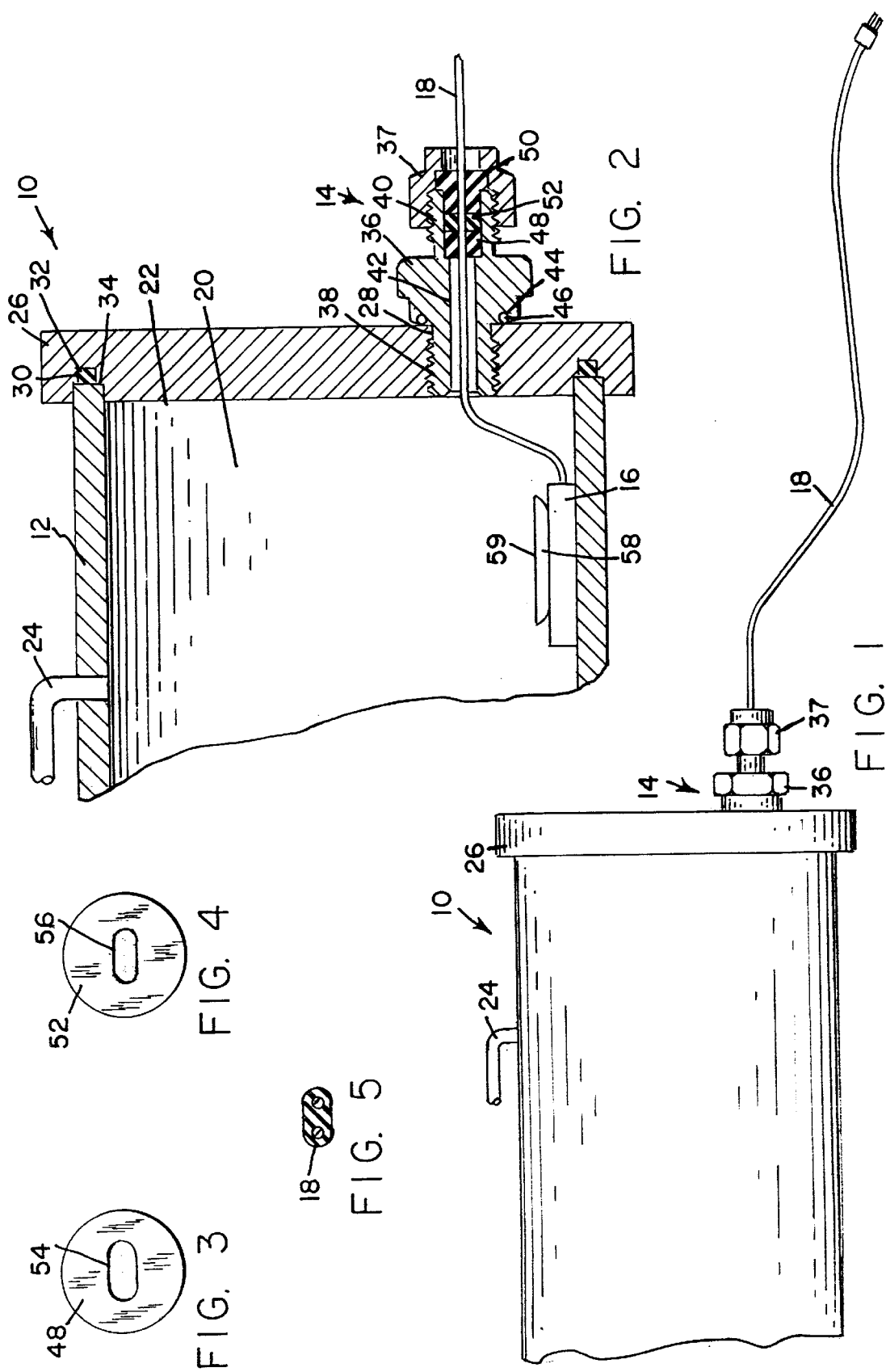

APPARATUS FOR AND METHOD OF DEVELOPING FINGERPRINTS

CROSS-REFERENCE TO RELATED APPLICATIONS

This application claims the benefit under 35 U.S.C. §119 (e) of prior U.S. Provisional Application No. 60/214,520 filed Jun. 28, 2000; which is hereby incorporated by reference.

STATEMENT REGARDING FEDERALLY SPONSORED RESEARCH OR DEVELOPMENT

This invention has been created without the sponsorship or funding of any federally sponsored research or development program.

BACKGROUND OF THE INVENTION

The present invention is generally directed to an apparatus for and a method of developing fingerprints and specifically with the use of cyanoacrylate (super glue).

The two methods which are currently in use for developing fingerprints with cyanoacrylate fuming either use heat and humidity or vacuum to accelerate the evaporization of the cyanoacrylate.

The use of heat or humidity with cyanoacrylate for developing fingerprints is the most common method currently in use. The process is simple, quick, inexpensive and produces durable latent prints on a variety of surfaces. However, there is a danger of overfuming if the articles of evidence bearing the fingerprints are not continually monitored during the fuming process. Also, the articles do not always fume evenly, especially articles with irregular surfaces, which includes most articles of evidence.

The vacuum method of cyanoacrylate fuming virtually eliminates the danger of overfuming and causes items to fume more evenly. Even items with very irregular surfaces, such as firearms or crumpled plastic bags, fume evenly. However, the fuming process requires more time (sometimes several hours), and it is difficult to monitor the process as the articles are usually out of view while in the vacuum. Results can be inconsistent and quite often items have to be re-fumed after the initial fuming and examination due to lack of development. The vacuum process also develops prints that are often less visible, and usually fluorescent dyes and a forensic light are needed to view prints. These and other difficulties experienced with the prior art coating systems have been obviated by the present invention.

It is, therefore, a principal object of the invention to provide a method of developing fingerprints which retains the advantages of the vacuum method of cyanoacrylate fuming and the heat method of cyanoacrylate fuming without the disadvantages of either prior method.

A further object of the invention is the provision of an apparatus for cyanoacrylate fuming which utilizes heat and vacuum.

Another object of the present invention is to provide an apparatus for cyanoacrylate fuming which produces clear fingerprints in a short amount of time and is easy to use.

With these and other objects in view, as will be apparent to those skilled in the art, the invention resides in the combination of parts set forth in the specification and covered by the claims appended hereto.

BRIEF SUMMARY OF THE INVENTION

In general, the invention consists of an apparatus for and method of developing fingerprints on an object by cyanoacrylate fuming. The apparatus includes a container having a chamber, an opening to the chamber and a mechanism for evacuating air from the chamber. The apparatus also includes a cover for hermetically sealing the opening, an exposed upper surface in the chamber for receiving drops of cyanoacrylate and an electrical heater for heating the exposed upper surface. More specifically, the electrical heater is located in the chamber and supports a receptacle which has the exposed upper surface. The electrical heater has an electrical cord that extends through a fixture which is attached to the cover. The cover, fixture and electrical cord are all sealed relative to the container to enable air to be evacuated from the chamber. The method of the present invention includes heating the receptacle, placing the object to be examined into the chamber, placing the receptacle in the chamber, placing a few drops of cyanoacrylate on the upper surface of the receptacle, applying the cover to the opening of the container, and pumping air from the chamber. The pump is then turned off. After the fuming of the cyanoacrylate, the cover is removed to remove the object from the chamber.

BRIEF DESCRIPTION OF THE DRAWINGS

The character of the invention, however, may be best understood by reference to one of its structural forms, as illustrated by the accompanying drawings, in which:

FIG. 1 is a side elevational view of an apparatus for developing fingerprints embodying the principle of the present invention;

FIG. 2 is a vertical longitudinal cross-sectional view of the apparatus of FIG. 1 on an enlarged scale;

FIG. 3 is an end view of an electrical insulator within the fixture that is connected to the cover of the container and through which the electrical cord extends;

FIG. 4 is an end view of an elastomeric disc which is also located within the fixture;

FIG. 5 is a cross-sectional view of the electrical cord; and

DETAILED DESCRIPTION OF THE INVENTION

Figure 6:
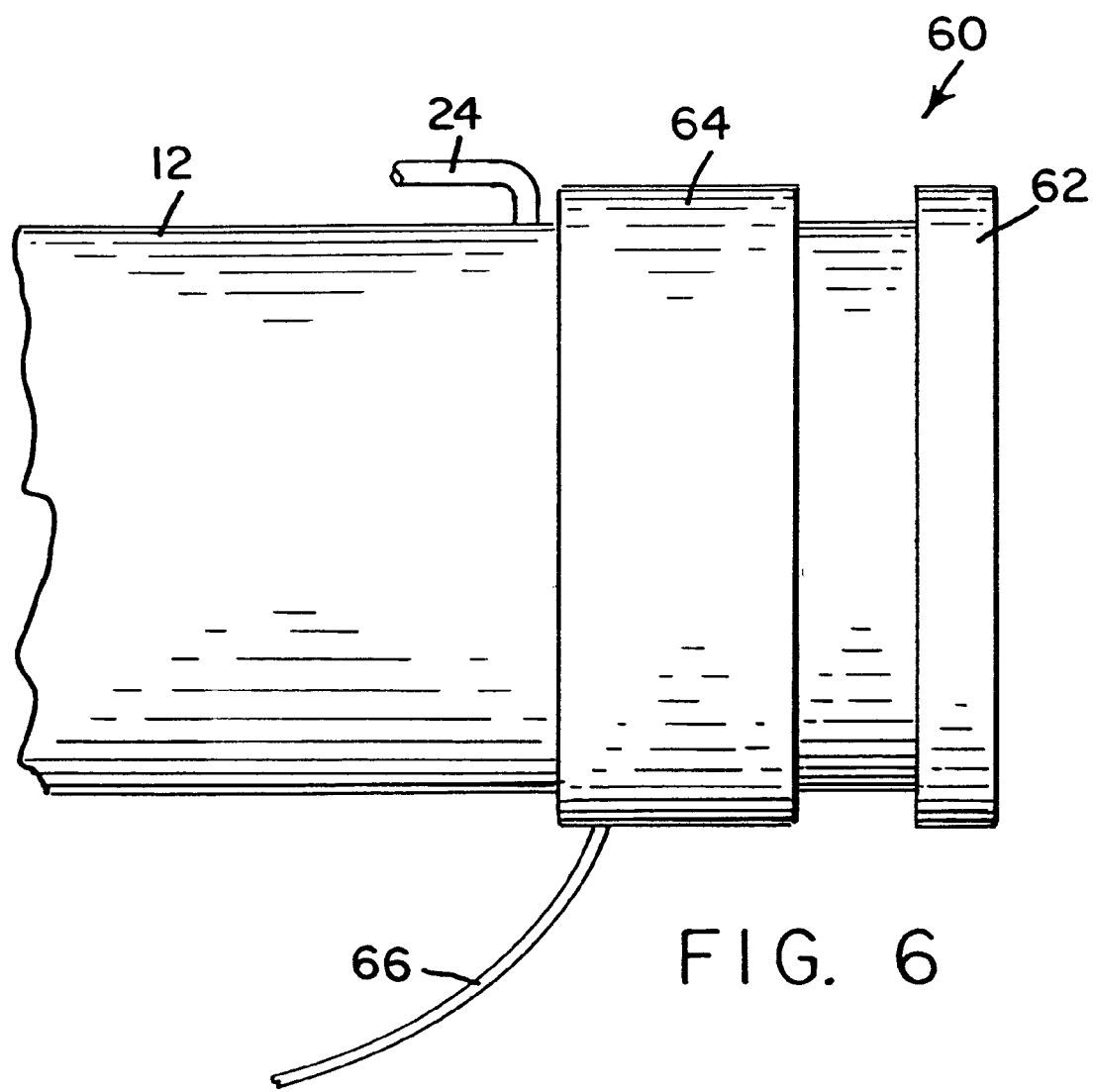
FIG. 6 is a side elevational view of a modified apparatus for developing fingerprints.

Referring first to FIGS. 1 and 2, there is shown the preferred apparatus, generally indicated by the reference numeral 10, for employing cyanoacrylate fuming to develop fingerprints. The preferred apparatus 10 includes a cylindrical tank or container 12, a fixture generally indicated by the reference numeral 14 which is connected to the container 12 and an electrical heater 16 which includes an electrical cord 18.

The container 12 has a chamber 20, an opening 22 to the chamber 20 at one end of the container, and an evacuation tube 24 connected to the chamber 20 and to a conventional vacuum pump, not shown. The Coleman Vacu-Print™ Long (rifle) Chamber sold by the Lightning Powder Company, Inc. (Catalog No. 1-4701) is an example of such a container. An example of a vacuum pump which has worked well is a Fast-Vac DV-85 with ½ HP and rated 3CFM sold by the Lightning Powder Company of Sahlem, Oregon. The opening 22 is closed by a removable cover 26 that has an annular groove 30. An elastomeric sealing ring or gasket 32 is located in the groove 30 for engaging an annular outer edge surface 34 at the open end of the container 12, for creating a seal between the cover 26 and the container 12. The cover 26 has a threaded bore 28.

The fixture 14 has a main body portion 36 and a nut portion 37. The main body portion 36 has a first nipple 38 threaded into the bore 28, and a second nipple 40 which extends away from the cover 26. The nipple 40 has external threads for receiving the nut portion 37. The fixture 14 has a cylindrical conduit 42 which contains an inner cylindrical insulator 48, an outer cylindrical insulator 50, and an elastomeric disc or washer 52 between the inner insulator 48 and the outer insulator 50. The portion of insulator 50 abutting disc 52 has the same diameter as the insulator 48. The remainder of the insulator 50 has a diameter which is substantially larger than that of the insulator 48. Both insulators 48 and 50 are made of a rigid electrically insulating material, preferably a fine-weave, cotton fabric based phenolic laminate sold under the trade name Garolite. The main body portion 36 has an annular groove 44 in the surface which abuts the cover 26. The groove 44 contains an annular elastomeric o-ring 46 for maintaining a seal between the fixture 14 and the cover 26. The electrical cord 18 from the heater 16 extends through the conduit 42, and through the insulators 48 and 50 and the washer 52 as shown in FIG. 2. The washer 52 thereby forms a seal between the electrical cord 18 and the fixture 14. The electrical cord 18 has a flat non-circular shape as shown in FIG. 5. Each of the insulators 48 and 50 has an aperture which is the same size and shape as the electrical cord 18. Insulator 48 has an aperture 54 as shown in FIG. 3. The insulator 50 has an aperture which is identical to that of insulator 48. The elastomeric disc or washer 52 has an aperture 56 which is similar in shape to that of the cord 18 but is considerably smaller to ensure an airtight seal between the cord 18 and the disc 52. When nut 37 is tightened on nipple 40, disc 52 is squeezed and also forms an airtight seal in the conduit 42.

Although many types of electric heaters can be used for heater 16, good results have been obtained with a coffee, soup, and beverage warmer, model 1400 sold by Dazey Corporation of New Century, KS. During the assembly of apparatus 10, the electrical cord 18 is disconnected from the heater 16. The cord 18 is then passed through insulator 50, disc 52, insulator 48 and conduit 42, and reconnected to the heater 16.

The apparatus 10 is used for developing fingerprints by, preferably, first turning the heater on. The cover 26 is removed from the container 12 and inserting the object to be examined for fingerprints is inserted within the chamber 20. A receptacle 58 having an upper control surface 59 is placed on the heater 16 and a few drops of cyanoacrylate is placed on the surface 59. The heater 16 and receptacle 58 are placed within the chamber 28 while simultaneously applying the cover 26 to the open end of the container. Air is evacuated from the chamber 20 by a pump and the pump is turned off. The heated container 58 accelerates the evaporation or fuming of the cyanoacrylate. The vacuum within the chamber 20 draws the cover 26 tightly against the outer edge surface 34 of the container 12 to maintain the cover tightly sealed against the container. After a period of time when it is believed that all of the cyanoacrylate has evaporated, or fumed, the chamber 20 is brought back to atmospheric pressure, which enables the cover 26 to be removed from the opening 22. This enables the object to be removed from the chamber 20 and examined for fingerprints. Alternatively, the heater can be turned on after the air has been evacuated from the chamber.

The fixture 14 can be applied to the side wall of a container by drilling a hole in the side wall of the container and tapping the hole. In the case of a cylindrical container such as container 12, the region around the hole is machined flat. Then fixture 14 can be seated flat to the outside of the container around the hole using o-ring 46 in groove 44. The o-ring will maintain a seal between the fixture 14 and apparatus 10.

Referring to FIG. 6, there is shown a modified apparatus generally indicated by the reference numeral 60. Apparatus 60 includes the chamber 12 and a cover 62 which is by identical to cover 26, except that it does not have a threaded bore 28. Apparatus 60 includes an electrical heater which is in the form of a flexible heating pad 64 wrapped around the exterior surface of the container 12, and includes an electrical cord 66. The procedure for developing fingerprints with the apparatus 60 is identical to that of apparatus 10 except that the heating step is provided by the heating pad 64 instead of the heater 16. By heating the container 12, a receptacle, such as the receptacle 58, located within the chamber 20 is also heated.

As a result of tests performed, fuming with cyanoacrylate using the heat and vacuum method gives the following advantages:

1. developed prints show excellent ridge detail;
2. there is no danger of over-development and background interference is virtually absent;
3. prints fume evenly, even on highly irregular surfaces;
4. the developed prints are durable and hold powders and dye stains well;
5. results are extremely consistent, as long as the method of application is performed consistently;
6. set-up is easy; and
7. fuming time is greatly reduced compared to conventional vacuum fuming.

The invention having been thus described, what is claimed as new and desired to secure by U.S. patent is:

1. Apparatus for developing fingerprints on an object comprising:
   (a) a container having a chamber for holding said object, an opening to said chamber and a mechanism for evacuating air from said chamber,
   (b) a cover removably connected to said container for hermetically sealing said opening;
   (c) an exposed upper surface within said chamber; and
   (d) an electrical heater for heating said exposed upper surface.

2. The apparatus as recited in said claim 1, wherein said container has an outer surface and said electrical heater is a pad in contact with said outer surface.

3. The apparatus as recited in claim 2, wherein said exposed upper surface is part of a receptacle and said electrical heater is located in said chamber in contact with said receptacle.

4. The apparatus as recited in claim 3, wherein said cover has a bore and said electrical heater has an electrical cord, said apparatus further comprising a fixture connected to said cover and at least partially occupying said bore, said electrical cord extending through said fixture.

5. Apparatus for developing fingerprints on an object comprising:
   (a) a container having a chamber, an opening to said chamber, a mechanism for evacuating air from said chamber;
   (b) a cover removably connected to said container for closing said opening, one of said cover and said container having a wall containing a bore;
   (c) a fixture connected to said cover, at least a portion of said fixture being located in said bore, said fixture having a conduit;

(d) an electrical heater located in said chamber;

(e) an electrical cord connected to said heater and extending through said conduit and having an electrical connector outside of said cover;

(f) a first seal between said container and said cover for forming a hermetic seal between said cover and said container;

(g) a second seal between said fixture and said wall for forming a hermetic seal between said wall and said fixture; and (h) a third seal between said fixture and said electrical cord for forming a hermetic seal between said fixture and said electrical cord, whereby subatmospheric pressure is created in said chamber when air is evacuated from said chamber.

6. The apparatus as recited in claim 5, wherein said cover has an annular groove facing said container and said first seal is a ring shaped gasket within said groove.

7. The apparatus as recited in claim 5, wherein at least one of said fixture and said wall has an outer surface containing an annular groove and said second seal is an elastomeric o-ring located in said groove.

8. The apparatus as recited in claim 5, wherein said third seal is an elastomeric disc having an aperture through which said electrical cord extends.

9. The apparatus as recited in claim 5, further comprising a receptacle in contact with said electrical heater, said receptacle having an exposed upper surface.

10. The apparatus as recited in claim 5, wherein said electrical cord is noncircular in cross section, and an interior portion of said fixture in contact with said electrical cord is a rigid electrical insulator located in said conduit, said insulator having an aperture which is substantially the same size and shape in cross section as the cross section of said electrical cord to enable said electrical cord to pass through said aperture without turning axially relative to said insulator.

11. The apparatus as recited in claim 5, wherein said opening is threaded and said fixture has a threaded nipple which is threaded into said opening.

12. A method of developing fingerprints on an object comprising the following steps:

(a) providing a container having a chamber, an opening to said chamber and a mechanism for evacuating air from said chamber;

(b) placing said object within said chamber through said opening;

(c) placing a receptacle within said chamber, said receptacle having an exposed upper surface;

(d) placing a plurality of drops of cyanoacrylate on said exposed upper surface;

(e) hermetically sealing said opening;

(f) evacuating air from said chamber; and (g) heating said receptacle to accelerate the evaporation rate of said cyanoacrylate.

13. The method as recited in claim 12, wherein said receptacle is heated by placing said receptacle on an electrical heater when said heater is in a non-heating state and actuating said electrical heater to a heating state after air has been evacuated from chamber.

14. The method as recited in claim 12, wherein said receptacle is heated by a heating said container after air has been evacuated from said container.

15. The method as recited in claim 12, wherein said container is heated by applying an electrical heating unit to the outside of said container.

16. A method of developing fingerprints on an object comprising the following steps:

(a) providing a container having a chamber, an opening to said chamber and a mechanism for evacuating air from said chamber;

(b) placing a receptacle within said chamber, said receptacle having an exposed upper surface;

(c) heating said receptacle;

(d) placing a plurality of drops of cyanoacrylate on said upper surface;

(e) placing said object within said chamber through said opening;

(f) hermetically sealing said opening;

(g) evacuating air from said chamber;

(h) after a period of time to allow said cyanoacrylate to evaporate, unsealing said opening; and (i) removing said object from said chamber for examination.

* * * * *

UNITED STATES PATENT AND TRADEMARK OFFICE
CERTIFICATE OF CORRECTION

PATENT NO.   : 6,423,946 B1
DATED         : July 23, 2002
INVENTOR(S)  : Berka et al.

It is certified that error appears in the above-identified patent and that said Letters Patent is hereby corrected as shown below:

Column 1,
Line 23, "evaporization" should be -- evaporation --.

Column 2,
Line 61, "Sahlem" should be -- Salem --.

Column 3,
Line 44, "inserting" should be deleted.
Line 47, "is" should be -- are --.

Column 4,
Line 7, "by" should be deleted.
Line 38, change "," (comma) to -- ; -- (semicolon).
Line 48, "2" should be -- 1 --.

Column 6,
Line 19, "a" should be deleted.

Signed and Sealed this

Seventeenth Day of February, 2004

JON W. DUDAS
*Acting Director of the United States Patent and Trademark Office*